US00PP29358P2

(12) United States Plant Patent
Rat

(10) Patent No.: US PP29,358 P2
(45) Date of Patent: Jun. 5, 2018

(54) ***PAEONIA* PLANT NAMED 'RTPIV791-01'**

(50) Latin Name: ***Paeonia lactiflora*×*P. lutea***
Varietal Denomination: RTPIV791-01

(71) Applicant: Thierry Rat, Moissac (FR)

(72) Inventor: Thierry Rat, Moissac (FR)

(73) Assignee: Planteck (CA)

( * ) Notice: Subject to any disclaimer, the term of this patent is extended or adjusted under 35 U.S.C. 154(b) by 0 days. days.

(21) Appl. No.: 15/530,472

(22) Filed: Jan. 19, 2017

(51) Int. Cl.
*A01H 5/02* (2006.01)

(52) U.S. Cl.
USPC ..... Plt./316

(58) Field of Classification Search
USPC ..... Plt./316
See application file for complete search history.

*Primary Examiner* — Annette H Para
(74) *Attorney, Agent, or Firm* — Cassandra Bright

(57) ABSTRACT

A new and distinct *Paeonia* cultivar named 'RTPIV791-01' is disclosed, characterized by distinctive creamy pale yellow suffused with pink, fully double, mildly fragrant flowers. Plants are vigorous and symmetrical with strong stems holding flowers above foliage, and with attractive foliage through the Fall. The new cultivar is a *Paeonia* hybrid suitable for ornamental garden purposes.

1 Drawing Sheet

Latin name of the genus and species: *Paeonia lactiflora*× *P. lutea*.

Variety denomination: 'RTPIV791-01'.

BACKGROUND OF THE INVENTION

The new cultivar is a product of a breeder program conducted by the inventor, Thierry Rat. This new variety, hereinafter referred to as 'RTPIV791-01', was discovered as part of a planned breeding program. The inventor, Thierry Rat, crossed the seed parent *Paeonia lactiflora* 'Miss America', unpatented, with the pollen parent, *Paeonia lutea* 'C36', unpatented, during May of 2006. The resulting new variety was selected in a research nursery in Castel Sarrasin France during May of 2012.

After identifying the new variety as a potentially interesting selection, the inventor first organized propagation of 'RTPIV791-01' by shoot tissue culture at a commercial laboratory in L'Assomption, Quebec, during September of 2012. The inventor continued controlled testing and propagation, assessing stability of the unique characteristics of this variety. Several generations have been reproduced and have shown that the unique features of this cultivar are stable and reproduced true to type.

SUMMARY OF THE INVENTION

The cultivar 'RTPIV791-01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'RTPIV791-01' These characteristics in combination distinguish 'RTPIV791-01' as a new and distinct *Paeonia* cultivar:

1. Strong stems which hold the flowers uniquely erect and above the foliage.
2. Unique creamy pale yellow suffused with pink, fully double flower.

3. Symmetrical, bushy plant shape.
4. Attractive foliage through Fall.

COMPARISON TO PARENT VARIETY

'RTPIV791-01' is similar in most horticultural characteristics to the seed parent variety *Paeonia lactiflora* 'Miss America'. Plants of the new cultivar 'RTPIV791-01' however, differ in the following characteristics:

1. 'Miss America' has a white, semi-double flowers, the new variety has a creamy pale yellow suffused with pink, fully double flower.
2. The new variety has stronger stems.
3. Foliage of the new variety is more finely cut.

'RTPIV791-01' is similar in most horticultural characteristics to the pollen parent variety *Paeonia lutea* 'C36'. Plants of the new cultivar 'RTPIV791-01' however, differ in the following characteristics:

1. 'C36' has yellow single to semi-double flowers, the new variety has creamy pale yellow suffused with pink, fully double flowers.
2. The new variety is a more herbaceous plant.
3. The new variety is more Winter hardy.

COMMERCIAL COMPARISON

'RTPIV791-01' can be compared to the commercial variety *Paeonia* 'Bartzella' unpatented. Plants of the new cultivar 'RTPIV791-01' are similar to plants of 'Bartzella' In most horticultural characteristics, as both are interspecific hybrid Peonies. Plants of the new cultivar 'RTPIV791-01' however, produce creamy pale yellow suffused with pink flowers, whereas flowers of 'Bartzella' are yellow with red centers. Plants of the new variety produce more secondary flower buds than plants of 'Bartzella'.

'RTPIV791-01' can be compared to the commercial variety *Paeonia* 'Morning Lilac' unpatented. Plants of the new cultivar 'RTPIV791-01' are similar to plants of 'Morning Lilac' in most horticultural characteristics, as both are interspecific hybrid *Paeonias*. Plants of the new cultivar 'RTPIV791-01' however, produce fully double, creamy pale yellow suffused with pink flowers, whereas flowers of 'Morning Lilac' are dark purple in color, with significantly less petals. Additionally, plants of the new variety have more secondary flower buds then 'Morning Lilac' plants.

BRIEF DESCRIPTION OF THE PHOTOGRAPH

The accompanying photograph illustrates in full color a typical flower of 'RTPIV791-01' grown outdoors in Moissac, France. The plant is approximately 5 years old.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'RTPIV791-01' plants grown outdoors in Moissac, France. Plants are approximately 5 year old. Measurements and numerical values represent averages of typical plant types.

Botanical classification: *Paeonia lactiflora*×*P. lutea* hybrid 'RTPIV791-01'.

PROPAGATION

Typically by shoot tissue culture.

Root description: Freely branching storage root with numerous feeder roots. Roots various shades of tan and brown, not accurately measured with a color chart.

PLANT

Growth habit: Compact and vigorous perennial herbaceous shrub. Symmetrical and rounded growth habit.

Height: Approximately 70 to 80 cm.

Plant spread: Approximately 100 cm.

Stems:

Length: Approximately 70 to 80 cm.

Diameter: Average 1 cm measured between first and second leaf.

Strength: Strong.

Internode length: 6 to 8 cm, highly variable.

Color: Near RHS Yellow-Green 144C.

Texture: Glabrous.

Age of plant described: Approximately 5 years.

FOLIAGE

Leaf: Alternate, bipinnately compound, with an overall ovate shape, which is wider than long. Average leaf 22 cm long and 27 cm wide. Erect attitude.

Leaflets:

*Shape*.—Broadly elliptic.

*Quantity and arrangement*.—3 primary leaflets further divided into secondary leaflets of variable number and form. All leaflets sessile.

*Average length*.—Central leaflet average 12 cm.

*Average width*.—Central leaflet average 12 to 14 cm.

Individual leaflet blades:

*Shape of blade*.—Broad elliptic, variably incised.

*Apex*.—Broadly acuminate, often with emargination.

*Base*.—Attenuate.

*Margin*.—Deeply incised.

*Texture of top surface*.—Glabrous.

*Texture of bottom surface*.—Glabrous.

*Appearance of top surface*.—Matte.

*Appearance of bottom surface*.—Matte.

*Aspect*.—Flat to very minutely reflexed downward.

*Color*.—Upper side: Near RHS Yellow-Green 143A. Under side: Near RHS Greyed-Green 191C.

*Venation*.—Type: Pinnate. Venation color upper side: Near RHS Yellow-Green 145D. Venation color under side: Near RHS Yellow-Green 145D.

*Petiole*.—Length: Average 6.0 cm. Diameter: 0.5 cm. Color: Near RHS Yellow-Green 144C. Texture: Glabrous.

FLOWER

Natural flowering season: Flowers open approximately 60 days after bud break in early Spring. Flowering extends over a period of 4 to 6 weeks.

Inflorescence type and habit: Single, terminal or axillary flowers, fully double, irregularly rounded with tight petal whorl. Erect flower attitude.

Flower longevity on plant: Approximately 8 to 12 days on the plant.

Quantity of flowers: 4 to 5 per stem.

Flower size:

*Diameter*.—Approximately 15 to 16 cm.

*Depth*.—Approximately 8 to 9 cm. (Flower height).

Peduncle:

*Length*.—Approximately 15 to 16 cm.

*Diameter*.—Approximately 0.6 cm.

*Color*.—Near RHS Yellow-Green 144C.

*Strength*.—Strong.

*Texture*.—Glabrous.

Petals:

*Petal arrangement*.—Tight, irregular whorl of about 50 petals and petaloids.

*Size*.—Length: Approximately 7 to 8 cm. Width: Approximately 6 to 7 cm.

*Shape*.—Obovate.

*Margin*.—Entire to sinuate.

*Apex*.—Typically emarginate.

*Base*.—Obtuse.

*Texture*.—Smooth, glabrous all surfaces.

*Aspect*.—Slightly ruffled, undulate.

Color: Petals: When opening: Fully opened: Upper surface: Near RHS Yellow 11A and 11B, suffused with Red 50D, base Orange-Red 32D. Lower surface: Near RHS Yellow 11A and 11B, suffused with Red 50D, base Orange-Red 32D.

Petaloids:

*Type*.—Stamenoidal.

*Quantity*.—Average 10 to 20, variable.

*Size*.—Length: Approximately 4.0 to 8.0 cm. Width: Approximately 0.5 to 1.0 cm.

*Color*.—Same as petals, near RHS Yellow 11A and 11B, base Orange-Red 32D.

Bud:

*Shape*.—Globose.

*Length*.—Approximately 5 cm.

*Diameter*.—Approximately 4 cm.

*Color*.—Near RHS Yellow-Green 145A.

Sepals:

*Quantity*.—5; 2 smaller and 3 larger.

*Length*.—Approximately 3.0 cm.

*Width*.—Approximately 3.0 cm.

*Shape*.—Obcordate to obovate.

*Aspect*.—Cupped.

*Apex*.—Mucronate.

*Margin*.—Entire.

*Color*.—Interior Surface: RHS Yellow-Green 144C. Exterior Surface: RHS Yellow-Green 144C.

*Texture*.—Glabrous.

Fragrance: Mild.

REPRODUCTIVE ORGANS

Stamens:

*Number*.—None observed.

Anthers: None.

Pistil:

*Type*.—Compound.

*Number*.—Average 6 to 7 carpels, variable.

*Carpel length*.—Approximately 2 cm.

*Stigma*.—Shape: Claw shaped; acutely convex. Color: Near RHS Orange-Red 32D.

*Ovary color*.—Near RHS Green 142D.

OTHER CHARACTERISTICS

Disease and pest resistance: Not observed to be susceptible nor resistant to normal diseases and pests of *Paeonia*.

Temperature tolerance: Typically USDA Zones 3 to 9.

Fruit/seed production: Not observed.

What is claimed is:

1. A new and distinct cultivar of *Paeonia* plant named 'RTPIV791-01' as herein illustrated and described.

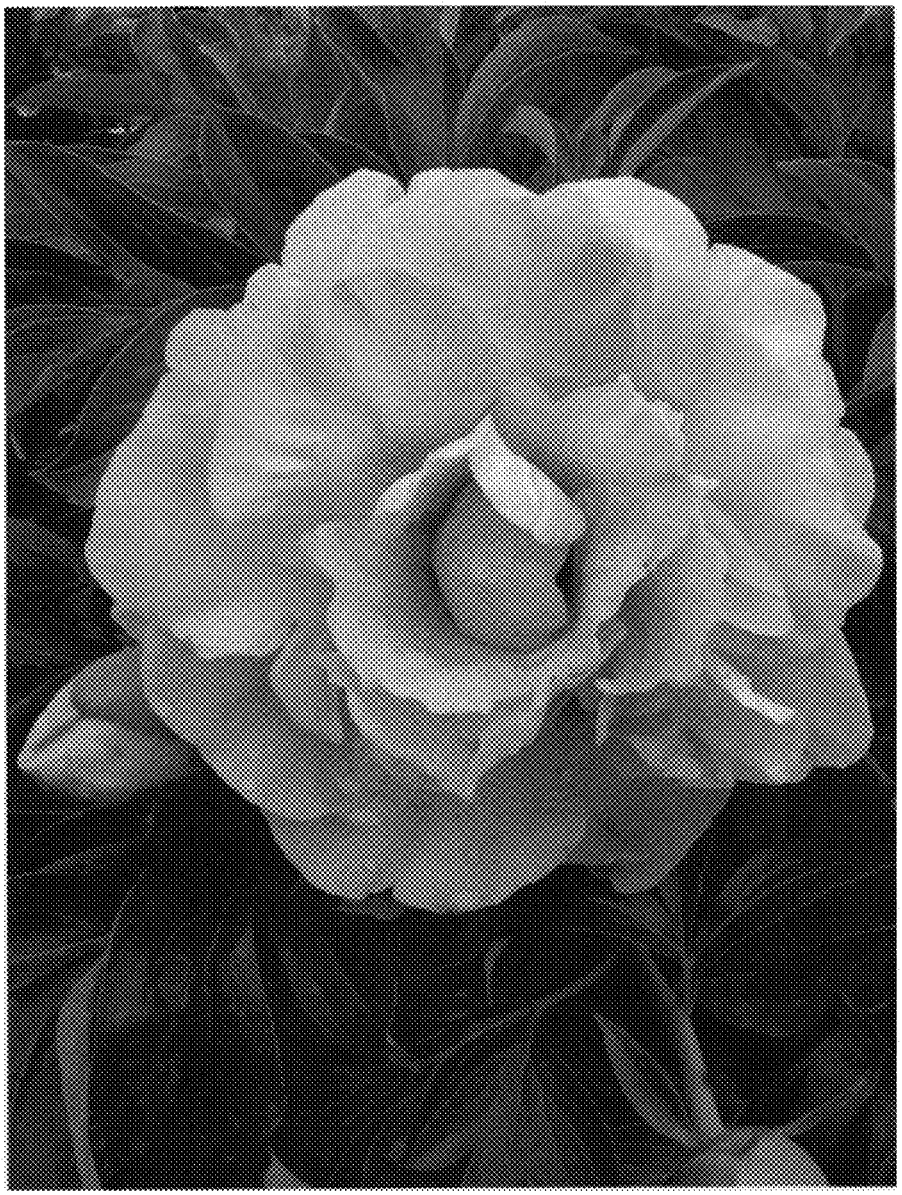

* * * * *